United States Patent [19]

Honda et al.

[11] Patent Number: 5,312,944

[45] Date of Patent: May 17, 1994

[54] ANTIBACTERIAL SILANE COUPLER COMPOUNDS CONTAINING GUANIDYL GROUP

[75] Inventors: Tsunetoshi Honda; Akiko Azuma; Akira Nishihara, all of Omiya, Japan

[73] Assignee: Mitsubishi Material Corporation, Tokyo, Japan

[21] Appl. No.: 996,987

[22] Filed: Dec. 24, 1992

[30] Foreign Application Priority Data

Dec. 28, 1991 [JP] Japan .................................. 3-359589
Dec. 28, 1991 [JP] Japan .................................. 3-359591

[51] Int. Cl.$^5$ ................................................ C07F 7/08
[52] U.S. Cl. .................................... 556/415; 556/414; 556/424
[58] Field of Search ......................... 556/414, 415, 424

[56] References Cited

U.S. PATENT DOCUMENTS

| | | | |
|---|---|---|---|
| 3,636,025 | 1/1972 | Barcza ................................. | 556/424 |
| 3,940,430 | 2/1976 | Brenner et al. ................. | 556/424 X |
| 4,248,993 | 2/1981 | Takago ........................... | 556/424 X |
| 4,954,598 | 9/1990 | Baglidachi et al. ............. | 556/424 X |
| 5,097,053 | 3/1992 | Baglidachi et al. ............. | 556/424 X |

FOREIGN PATENT DOCUMENTS

456093A2  4/1991  European Pat. Off. .
460385A2  4/1991  European Pat. Off. .

*Primary Examiner*—Paul F. Shaver
*Attorney, Agent, or Firm*—David G. Conlin; Linda M. Buckley

[57] ABSTRACT

Novel silane coupler compounds having antibacterial activity are disclosed. Biguanidyl group or cyanoguanidyl group is introduced into silane coupler compounds.

3 Claims, No Drawings

ANTIBACTERIAL SILANE COUPLER COMPOUNDS CONTAINING GUANIDYL GROUP

FIELD OF THE INVENTION

The present invention relates to a class of novel silane coupler compounds containing a guanidyl group, which are useful as antibacterial agents and processes for preparation thereof.

The compounds of this invention are useful as germicides, algicides, antibacterial agents, antimold agents, deodorizers, fiber treatment agents having antiseptic activity, resin modifiers, water repellents, cosmetic materials, mold releases, paint additives, etc.

BACKGROUND OF THE INVENTION

Hydrolyzable organic silane compounds chemically combine with glass, ceramics, wood, paper, fibers, resins and other various materials and are widely used as silane couplers in various industrial fields.

It has been attempted to introduce antibacterial groups into silane coupler compounds and to provide the surface of various materials with antibacterial activity utilizing chemical affinity of silane coupler compounds to various materials. By fixing antibacterial moieties of the compounds to the surface of various materials, the materials are provided with long lasting antibacterial activity free from danger of environmental pollution. This will reduce appearance of antibiotic-resistant strains and enable disinfection of a large amount of materials and continuous disinfection.

Silane compounds having a quaternary ammonium salt in their molecule as an antibacterial moiety were proposed (JP2-6489A). However, quaternary ammonium salt is an ionic compound and thus influenced by coexisting inorganic salts, sugars, proteins, etc. losing antibacterial activity or suffering discoloration. The active polar portion thereof is small in comparison with the alkyl chain in the molecule, and, therefore, when it is applied to the surface of fibers for instance, the fiber surface become water repellent because of introduction of the long chain alkyl group, that is, the fibers lose their inherent hygroscopic property. In the case of woven fabric, water or steam permeability and impregnation property thereof are impaired. Therefore, there has been a demand for a compound which can provide fibers with long-lasting excellent antibacterial activity without impairing inherent hydrophilicity of fibers.

Many and various antibacterial substances are known including quaternary ammonium compounds. Guanidyl compounds, which are known to have biological activity such as antimalarial, are examples of such compounds.

However, the mechanism of germicidal activity of these compounds is not yet quite clearly understood and presence of a specific group does not always cause germicidal activity. It is well known that biological activity of biguanide compounds remarkably varies depending on the species of substituents. (Refer to: J. Chem. Soc., 729 (1946).

The object of the present invention is to provide compounds which will solve problems of antibacterial-activity-providing compounds and are able to provide a wide range of materials with long-lasting antibacterial activity.

We prepared a class of novel compounds, which comprise a hydrolyzable silane coupler compound at the molecular end of which a guanidyl group is attached and found that some of them have strong germicidal activity and are practically useful as antibacterial agents. These compounds have excellent hydrophilicity and have no ionic moiety and thus the above described problems are unexpectedly solved at one effort. Thus we completed this invention.

DISCLOSURE OF THE INVENTION

The present invention provides silane coupler compounds represented by the formula (I):

XSi(CH$_2$)$_n$(NH(CH$_2$)$_2$)$_m$G wherein X is a halogen or a C1–C5 alkoxy group, n is an integer of 1–6, m is an integer of 0 or 1 and G is a cyanoguanidyl or biguanidyl group, which may be substituted with a C1–C8 alkyl, a phenyl, which may be substituted with halogen, a C1–C4 alkyl or fluoromethyl, or a salt thereof.

Of halogens, chlorine is preferred because of hydolyzability. Of alkoxy groups, methoxy and ethoxy are preferred. Alkoxy groups, whose alkyl group is larger than C5, will impair the hydrophilicity. The compounds, wherein G is a biguanidyl group can be a salt of an organic acid such as acetic acid, citric acid, gluconic acid, etc. or an inorganic acid such as hydrochloric acid, sulfuric acid, etc.

By selecting the substituent attached to the biguanide group, antibacterial property and spectrum can be varied. Substitution in the guanidyl group with hydrogen, C1–C20 alkyl or phenyl, which may be substituted with a group selected from halogen, alkyl, fluoroalkyl and alkoxy, will give better antibacterial activity.

Typical examples of the compounds of the present invention are as follows:

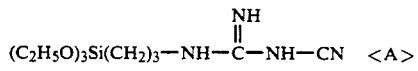

(C$_2$H$_5$O)$_3$Si(CH$_2$)$_3$—NH—C(=NH)—NH—CN    <A>

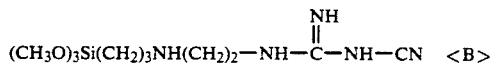

(CH$_3$O)$_3$Si(CH$_2$)$_3$NH(CH$_2$)$_2$—NH—C(=NH)—NH—CN    <B>

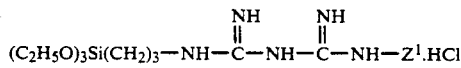

(C$_2$H$_5$O)$_3$Si(CH$_2$)$_3$—NH—C(=NH)—NH—C(=NH)—NH—Z$^1$·HCl

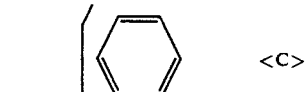
<C>

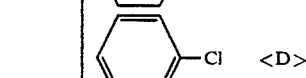
<D>

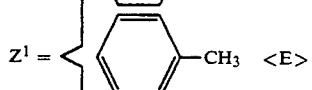
Z$^1$ = <E>

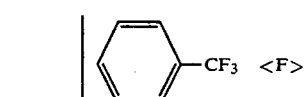
<F>

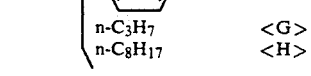
n-C$_3$H$_7$    <G>
n-C$_8$H$_{17}$    <H>

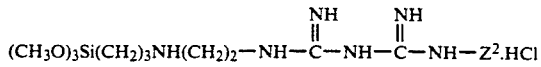

(CH$_3$O)$_3$Si(CH$_2$)$_3$NH(CH$_2$)$_2$—NH—C(=NH)—NH—C(=NH)—NH—Z$^2$·HCl

-continued

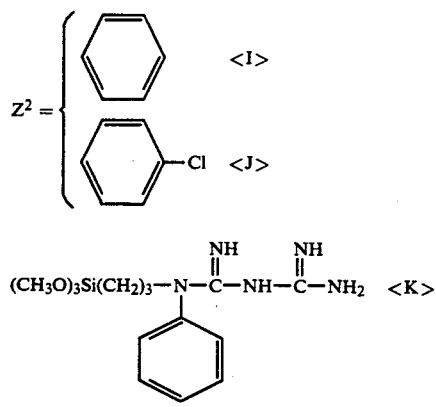

The present invention also provides a process for preparation of the compounds of the above formula (I), wherein G is a cyanoguanidyl group, comprising reacting a compound of formula (II):

$$XSi(CH_2)_n(NH(CH_2)_2)_mNH_2$$

wherein n and m are as defined above, with a compound of formula::

$$NC-N=C(SCH_3)NH_2$$

or $$NaN(CN)_2.$$

Of the compounds $XSi(CH_2)_n(NH(CH_2)_2))_mNH_2$, a compound $XSi(CH_2)_3NH_2$ is commercially available.

The reaction of the above aminosilane compound and the above nitrile should be conducted in a solvent stable to the hydrolyzable silyl group. Alcohols, acetones, benzene and toluene, which have been well The present invention also provides a process for preparation of the compounds of the above formula (I), wherein G is a biguanidyl group, comprising reacting a compound of formula (I):

$$XSi(CH_2)_n(NH(CH_2)_2)_mG$$

wherein n and m are as defined above and G is a cyanoguanidyl, with an amine compound of formula:

$$ZNH_2$$

wherein Z is hydrogen, C1-C20 alkyl or phenyl, which may be substituted with halogen, alkyl, fluoroalkyl or alkoxy.

The biguanidyl group can be a salt with an organic acid such as acetic acid, citric acid, gluconic acid, etc. or an inorganic acid such as hydrochloric acid sulfuric acid, etc. The salts can be easily converted to the base by treating a base.

By selecting species of substituents to be attached to the guanidyl group, germicidal effect and antibacterial spectrum of the compound can be varied. The substituent should preferably be any of hydrogen, C1-C20 alkyl or phenyl, which may be substituted with halogen, alkyl, fluoroalkyl and alkoxy.

The reaction temperature is 0°–200° C., preferably 60°–150° C. The reaction time depends on reaction conditions, reactivity of the reactants, etc.

The surface treatment with these compounds of the present invention can be carried out in the same manner as in the case of known silane couplers. According to the conditions of practical application, the compounds can be diluted with a suitable solvent or can be heat-treated after application.

The compounds of the present invention can be applied to the surface of any material which is combinable with silane couplers. They are especially useful in the domain where application of organic antibacterial silane couplers was difficult so far. Specifically, the compound will exhibit practical value in application to sport wear, under wear including socks and stockings, bedding; rugs, mats or tiles used in the kitchen and the bathroom. The materials treated with the compounds, can be dyed. In this case, it is expected that dyability of fabric with hydrophilic dyes will be improved.

SPECIFIC DESCRIPTION OF THE INVENTION

Now the invention will be illustrated by way of working examples. Compounds A–K prepared in Example 1–11 are the above described Compounds A–K.

EXAMPLE 1

Preparation of Compound A

In a 100 ml three-necked flask equipped with a stirrer, a thermometer, a refluxing apparatus and a nitrogen inlet, 10.0 g (45 mmol) of gamma-aminopropyltriethoxysilane "KBE-903" (marketed by Shin'etsu Kagaku Kogyo KK), 5.2 g (45 mmol) of NC—N=C(SCH_3)NH_2 and 50 ml of ethanol were placed and the reaction mixture was refluxed for 18 hours in a nitrogen atmosphere. Thus, 13.1 g of light yellow oily substance was obtained after the solvent was distilled away under reduced pressure.

This substance was dissolved in 300 ml of water so that the concentration was 0.5 wt%. 30 g of knitted cotton fabric was immersed in this solution and the solution was slowly stirred for 1 hour. Thereafter the fabric was squeezed until the water content was 100 % and dried at 90° C. for 15 minutes.

The resulting fabric was tested for evaluation of its antibacterial activity in accordance with the AATCC-100 test using Klebsiella pneumoniae. Also its water absorption was tested in accordance with JIS L-1018A.

The results are shown in Table 1.

EXAMPLE 2

Preparation of Compound B

Using 10 g (45 mmol) of N-beta(aminoethyl)-gamma-aminopropyltrimethoxysilane "KBM-603" (marketed by Shin'etsu Kagaku Kogyo KK) instead of gamma-aminopropyltriethoxysilane, the procedures of Example 1 were repeated and 13.4 g of light yellow oily substance was obtained.

The obtained substance was used for treatment of the same cotton fabric and tested in the same manner as in Example 1.

The results are shown in Table 1.

COMPARATIVE EXAMPLE 1

The same fabric was treated with gamma-aminopropylethoxysilane and tested for antibacterial activity and water absorption in the same manner as in Example 1. The results are shown in Table 1.

COMPARATIVE EXAMPLE 2

The same fabric was treated with N-beta-(aminoethyl)-gamma-aminopropyltrimethoxysilane and tested for antibacterial activity and water absorption in the same manner as in Example 1.

The results are shown in Table 1.

COMPARATIVE EXAMPLE 3

The same fabric was treated with trimethoxysilylpropyldimethyloctadecylammonium chloride (silyl quaternary ammonium salt compound)e and tested for antibacterial activity and water absorption in the same manner as in Example 1.

The results are shown in Table 1.

COMPARATIVE EXAMPLE 4

The same fabric which was not treated with an antibacterial substance was tested for antibacterial activity and water absorption in the same manner.

The results are shown in Table 1.

EXAMPLE 3

Preparation of Compound C

In a 100 ml three necked flask equipped with a stirrer, a thermometer, a refluxing apparatus and a nitrogen inlet, 5 g (17.4 mmol) of the product of Example 1, 2.3 g (17.4 mmol) of aniline hydrochloride and 50 ml of ethanol were placed and the reaction mixture was refluxed for 20 hours in a nitrogen atmosphere. Thus, 6.8 g of light yellow solid substance was obtained after the solvent was distilled away under reduced pressure. This substance was recrystallized from ethyl acetate, collected by filtration and dried in a thermostatic dryer at 100° C. for 2 hours. Thus 5.3 g of white solid substance was obtained.

This substance was dissolved in 300 ml of water so that the concentration was 0.5 wt%. 30 g of knitted cotton fabric was immersed in this solution and the solution was slowly stirred for 1 hour at 60° C. The fabric was squeezed until the water content became 100 % and dried at 90° C. for 15 minutes.

The resulting fabric was tested for evaluation of antibacterial activity and water absorption in accordance with AATCC-100 and JIS L-1018 Method A.

The results are shown in Table 1. in Example 1.

EXAMPLE 4

Preparation of Compound D

Using 2.9 g (17.4 mmol) of p-chloroaniline instead of aniline hydrochloride, the procedures of Example 3 was repeated and 5.8 g of white solid substance was obtained.

This substance was tested for antibacterial activity and water absorption in the same manner as in Example 3.

The results are shown in Table 1.

EXAMPLE 5

Preparation of Compound E

Using 2.5 g (17.4 mmol) of p-methylaniline instead of aniline hydrochloride, the procedures of Example 3 was repeated and 4.2 g of white solid substance was obtained.

This substance was tested for antibacterial activity and water absorption in the same manner as in Example 3.

The results are shown in Table 1.

EXAMPLE 6

Preparation of Compound F

Using 3.4 g (17.4 mmol) of p-trifluoromethylaniline instead of aniline hydrochloride, the procedures of Example 3 was repeated and 6.1 g of white solid substance was obtained.

This substance was tested for antibacterial activity and water absorption in the same manner as in Example 3.

The results are shown in Table 1.

EXAMPLE 7

Preparation of Compound G

Using 1.7 g (17.4 mmol) of n-propylamine instead of aniline hydrochloride, the procedures of Example 3 was repeated and 3.8 g of white solid substance was obtained.

This substance was tested for antibacterial activity and water absorption in the same manner as in Example 3.

The results are shown in Table 2.

EXAMPLE 8

Preparation of Compound H

Using 2.4 g (17.4 mmol) of n-hexylamine instead of aniline hydrochloride, the procedures of Example 3 was repeated and 5.0 g of white solid substance was obtained.

This substance was tested for antibacterial activity and water absorption in the same manner as in Example 3.

The results are shown in Table 1.

EXAMPLE 9

Preparation of Compound I

In a 100 ml three-necked flask equipped with a stirrer, a thermometer, a refluxing apparatus and a nitrogen inlet, 5.0 g (17.4 mmol) of the product of Example 2, 2.3 g of aniline hydrochloride and 50 ml of ethanol were placed and the reaction mixture was refluxed for 26 hours in a nitrogen atmosphere. Thus, 6.2 g of light yellow solid substance was obtained after the solvent was distilled away under reduced pressure. This substance was recrystallized from ethyl acetate, collected by filtration and dried in a thermostatic drier at 100° C. for 2 hours. Thus 4.8 g of a white solid substance was obtained.

The resulting substance was used for treating the same fabric and was tested for evaluation of antibacterial activity and water absorption in the same manner as in Example 1.

The result is shown in Table 1.

EXAMPLE 10

Preparation of Compound J

Using 2.9 g (17.4 mmol) of p-chloroaniline instead of aniline hydrochloride, the procedures of Example 9 was repeated and 4.9 g of white solid substance was obtained.

This substance was tested for antibacterial activity and water absorption in the same manner as in Example 3.

The results are shown in Table 1.

EXAMPLE 11

Preparation of Compound K

In a 100 ml three-necked flask equipped with a stirrer, a thermometer, a refluxing apparatus and a nitrogen inlet, 6.7 g (17.4 mmol) of gamma-chloropropylmethoxysilane, 6.0 g (34 mmol) of 1-phenylbiguanide and 50 ml of acetone were placed and the reaction mixture was refluxed for 105 hours in a nitrogen atmosphere. Thus, 11.7 g of light yellow solid substance was obtained after the solvent was distilled away under reduced pressure. This substance was recrystallized from ethyl acetate, collected by filtration and dried in a thermostatic drier at 100° C. for 2 hours. Thus 7.3 g of a white solid substance.

The resulting substance was used for treating the same fabric and was tested for evaluation of antibacterial activity and water absorption in the same manner as in Example 3.

The result is shown in Table 1.

TABLE 1

| Compound | Sterilization (%) | Water Absorption |
| --- | --- | --- |
| Ex. 1 | 86.5 | 0 |
| Ex. 2 | 81.6 | 1 |
| Ex. 3 | 94.5 | 0 |
| Ex. 4 | 99.9 | 0 |
| Ex. 5 | 84.5 | 2 |
| Ex. 6 | 99.9 | 2 |
| Ex. 7 | 78.5 | 1 |
| Ex. 8 | 91.3 | 3 |
| Ex. 9 | 83.7 | 1 |
| Ex. 10 | 95.6 | 1 |
| Ex. 11 | 90.1 | 0 |
| Comp. Ex. 1 | 0 | 1 |
| Comp. Ex. 2 | 1.2 | 1 |
| Comp. Ex. 3 | 88.2 | 600< |
| Comp. Ex. 4 | 0 | 0 |

The antibacterial compounds of the present invention can provide various materials with germicidal and antibacterial properties. Further, as the compounds have high hydrophilicity and, therefore, the characteristics cannot be impaired even if the substrate (wood, for instance) has high hydrophicity.

What we claim is:

1. Silane coupler compounds represented by the formula (I):

$$XSi(CH_2)_n(NH(CH_2)_2)_mG$$

wherein X is a halogen or a C1–C5 alkoxy group, n is an integer of 1–6, m is an integer of 0 or 1 and G is a cyanoguanidyl or biguanidyl group, which may be substituted with a C1–C8 alkyl, a phenyl, which may be substituted with halogen, a C1–C4 alkyl or fluoromethyl, or a salt thereof.

2. Process for preparation of the compounds of formula (I), $$XSi(CH_2)_n(NH(CH_2)_2)_mG$$

wherein X is a halogen or a C1–C5 alkoxy group, n is an integer of 1–6, m is an integer of 0 or 1 and G is a cyanoguanidyl, comprising reacting a compound of formula (II):

$$XSi(CH_2)_n(NH(CH_2)_2)_mNH_2$$

with a compound of formula:

$$NC-N=C(SCH_3)NH_2$$

or $$NaN(CN)_2.$$

3. Process for preparation of the compounds of the formula (I):

$$XSi(CH_2)_n(NH(CH_2)_2)_mG$$

wherein X is a halogen or a C1–C5 alkoxy group, n is an integer of 1–6, m is an integer of 0 or 1 and G is a biguanidyl group, which may be substituted with a C1–C8 alkyl, a phenyl, which may be substituted with halogen, a C1–C4 alkyl or fluoromethyl, or a salt thereof, comprising reacting a compound of formula (I):

$$XSi(CH_2)_n(NH(CH_2)_2)_mG$$

wherein G is a cyanoguanidyl, with an amine compound of formula:

$$ZNH_2$$

wherein Z is hydrogen, C1–C20 alkyl or phenyl, which may be substituted with halogen, alkyl, fluoroalkyl or alkoxy.

* * * * *